US007597101B2

(12) United States Patent
Burnett et al.

(10) Patent No.: US 7,597,101 B2
(45) Date of Patent: Oct. 6, 2009

(54) METHOD AND APPARATUS FOR PERSONAL ISOLATION AND/OR PROTECTION

(75) Inventors: Daniel Rogers Burnett, San Francisco, CA (US); Shane Mangrum, Ammon, ID (US)

(73) Assignee: TheraNova, LLC, San Francisco, CA (US)

( * ) Notice: Subject to any disclaimer, the term of this patent is extended or adjusted under 35 U.S.C. 154(b) by 638 days.

(21) Appl. No.: 11/332,799

(22) Filed: Jan. 17, 2006

(65) Prior Publication Data

US 2007/0163586 A1 Jul. 19, 2007

(51) Int. Cl.
*A61M 11/00* (2006.01)

(52) U.S. Cl. .................................................. 128/204.18

(58) Field of Classification Search ............ 128/204.18, 128/206.12, 204.21, 206.21; 600/21
See application file for complete search history.

(56) References Cited

U.S. PATENT DOCUMENTS 3,976,063 A * 8/1976 Henneman et al. ..... 128/201.25
4,172,454 A * 10/1979 Warncke et al. ........ 128/201.29
4,846,166 A * 7/1989 Willeke ................. 128/200.24
2003/0005934 A1* 1/2003 Japuntich et al. ....... 128/206.15

* cited by examiner

*Primary Examiner*—Steven O Douglas
(74) *Attorney, Agent, or Firm*—Levine Bagade Han LLP

(57) ABSTRACT

The present invention may create and maintain a pressure differential in the vicinity of the user's nasopharynx. A portable filter and pressurized air source subjects the region of the user's nasopharynx to positive or negative pressured air. Positive pressure prevents exposure to surrounding air while negative pressure isolates those around the user from potential toxins or pathogens exhaled from the user. With positive pressure, surrounding air is displaced preventing exposure to ambient air in most instances. With negative pressure, exhaled air is evacuated from the nasopharynx, filtered and returned to the user's surroundings to prevent exposure to those around the user. Such devices may be incorporated into garments, accessories or existing isolation devices (e.g., face masks) to improve efficacy. Alternatively, the device may also be attached to an air source in the user's vicinity and provide filtration of the air prior to delivery to the region surrounding the user.

19 Claims, 7 Drawing Sheets

METHOD AND APPARATUS FOR PERSONAL ISOLATION AND/OR PROTECTION

BACKGROUND OF THE INVENTION

The present invention relates to the field of medical devices, in particular personal isolation and/or protection devices to reduce the risk of airborne illness transmission.

Prior to the present invention, various isolation devices have been contemplated, including passive face masks, gas masks and some tent-based devices. For the purposes of traveling where one will frequently interact with others and be exposed to their secretions, the face and gas masks are either too bulky or ineffective and the tent-based devices are not practical. Regarding face masks, in particular, even with professional installation these masks are notoriously poor at preventing airborne illness transmission. Gas mask provide a better system for filtration and can accomplish effective isolation, but are very bulky, awkward and unattractive. Furthermore, for longer trips, the gas mask must be removed to allow for drinking and eating which negates the purpose for such a device. Tent-based devices, while highly effective when used in combination with positive pressure, are not at all practical for use outside of the home or office. Therefore, there exists a strong need, particularly in light of the upcoming flu epidemic, for a less obtrusive, more effective personal isolation system.

SUMMARY OF THE INVENTION

The device of the present invention may create and maintain a pressure differential in the vicinity of the user's nasopharynx. Using a portable filter and pressurized air source, the region of the user's nasopharynx can be subjected to positive or negative pressured air. Positive pressure will prevent exposure surrounding air while negative air pressure will isolate those around the user from potential toxins or pathogens exhaled from the user. In the positive pressure embodiments, the surrounding air may be displaced by the positive pressure environment preventing exposure to ambient air in all instances other than a direct blast of high flow air directed at the users nasopharynx (such as an uncovered and maliciously directed sneeze). If adequate pressure is used, though, even this scenario would not allow for transmission of airborne illness with repulsion of any infective droplets being repelled by the positive pressure created. In the negative pressure embodiment, exhaled air may be evacuated from the nasopharynx, filtered and returned to the user's surroundings to prevent exposure to those around the user. The device of the present invention may be incorporated into a variety of garments, accessories or existing isolation devices (ie face masks) to improve their efficacy. Alternatively, the device may also be attached to an air source in the user's vicinity and simply provide filtration of the air prior to delivery to the region surrounding the user.

In the positive pressure embodiment, the positive pressure and/or repelling force could be generated by a variety of mechanisms, but in its preferred embodiment includes a filter, a fan (or pressurized air source), a head and/or neck worn garment to direct the airflow to create the localized positive pressure region and optional tubing to channel air flow if the fan/filter is not incorporated directly into a head or neck worn garment.

The device could be used in combination with a face mask to drastically increase its efficacy, as well, by creating a positive pressure environment between the face mask and the nasopharynx to prevent ambient air and water droplets from passing around the edges of the mask into the user's lungs (the most common failure mechanism).

Lastly, in the airplane embodiment or in any area where a pressurized air source is available, the device may consist of a hepa or other filter which may be reversibly or irreversibly attached to the pressurized air source to generate a localized positive pressure region of sterilized air. This embodiment may be used in combination with a partial or full canopy, as well, in order to increase the local positive pressure generation around the user.

The present invention may be constructed of a variety of materials and may be used for a variety of applications with the only requirement being that of portable, localized positive pressure generation for the protection of the user. Applications include protection for air travelers, healthcare workers, construction workers or any other application in which the user desires to prevent exposure to ambient air and its constituent toxins and pathogens.

Alternatively, particularly for air and other forms of travel, the device of the present invention could also be modified to provide for isolation of the user's surrounding from the users exhaled air. In this embodiment, capable of being used with a face mask as well, the filtration mechanism may draw air from the region of the patient's nasopharynx creating a localized region of negative pressure to prevent transmission of exhaled particles from the user to anyone in their vicinity. This embodiment may be used in a variety of applications, as well, with quarantine of infected traveling individuals and prevention of transmission of pathogens from visitors to immunocompromised patients being two robust applications. In this way, the use of a portable negative pressure isolation system, the user need not worry about infecting or exposing individuals in their vicinity.

DETAILED DESCRIPTION OF THE DRAWINGS

Figure 1:
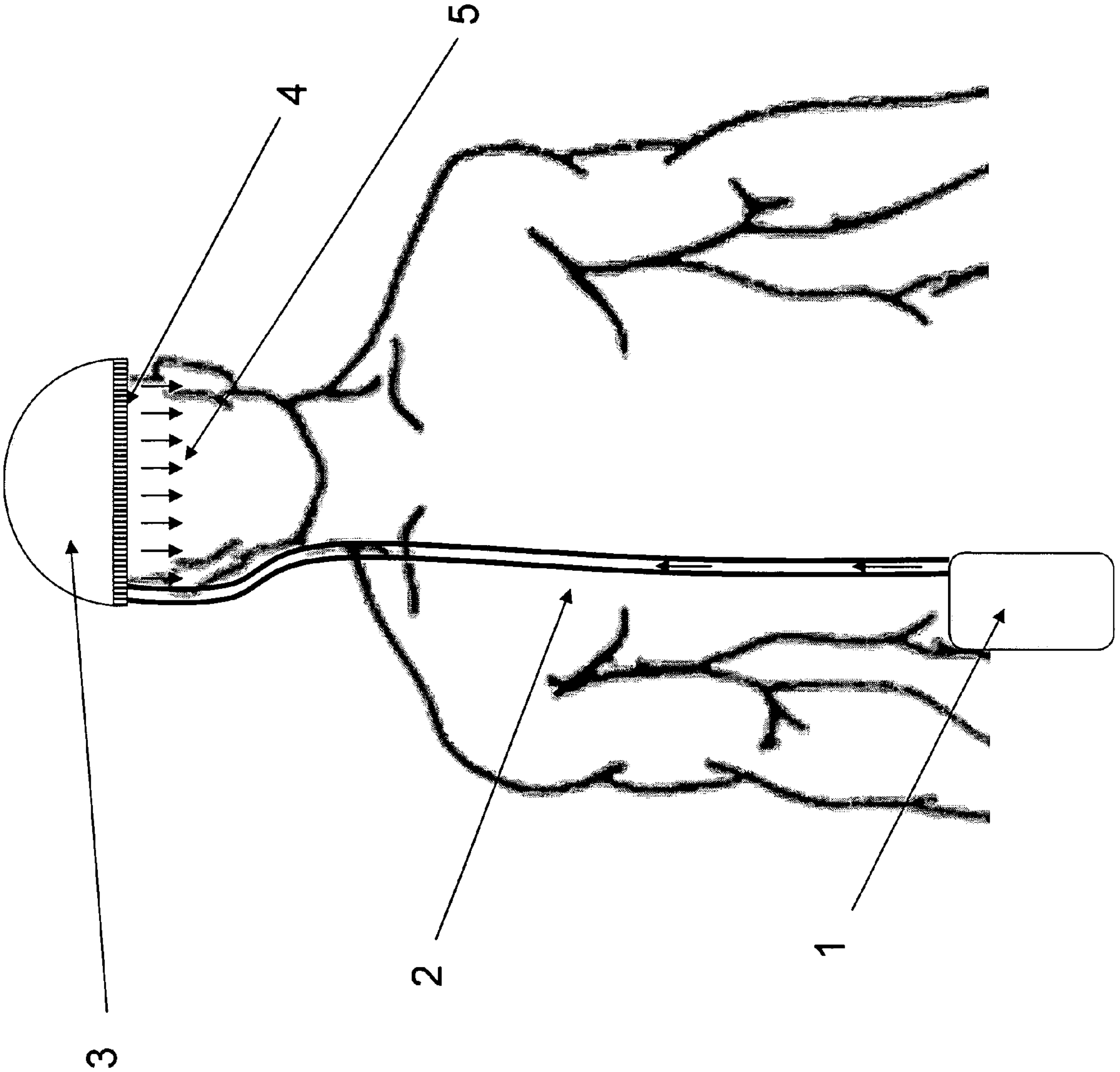
FIG. 1 is a perspective view of the cap-worn embodiment of the present invention.

The present invention may take a variety of embodiments with the only requisite feature being that of a portable, air filter capable of generating a localized pressure differential in the region of the user's nasopharynx. As can be seen in FIG. 1, the device may consist of a Air filter/air source 1 which may or may not be in a single unit. The device may further consist of optional tubing 2 and air channels 4 to create pressure differential 5 in the region of the user's nasopharynx. In FIG. 1, an embodiment is illustrated wherein said device utilizes a headworn garment 3, to focus the positive pressure to the region of the user's nasopharynx. In this case, and with all other embodiments, while only one pressure differential is illustrated (in this case positive pressure) the opposite differential may also be used (ie negative pressure).

Figure 2:
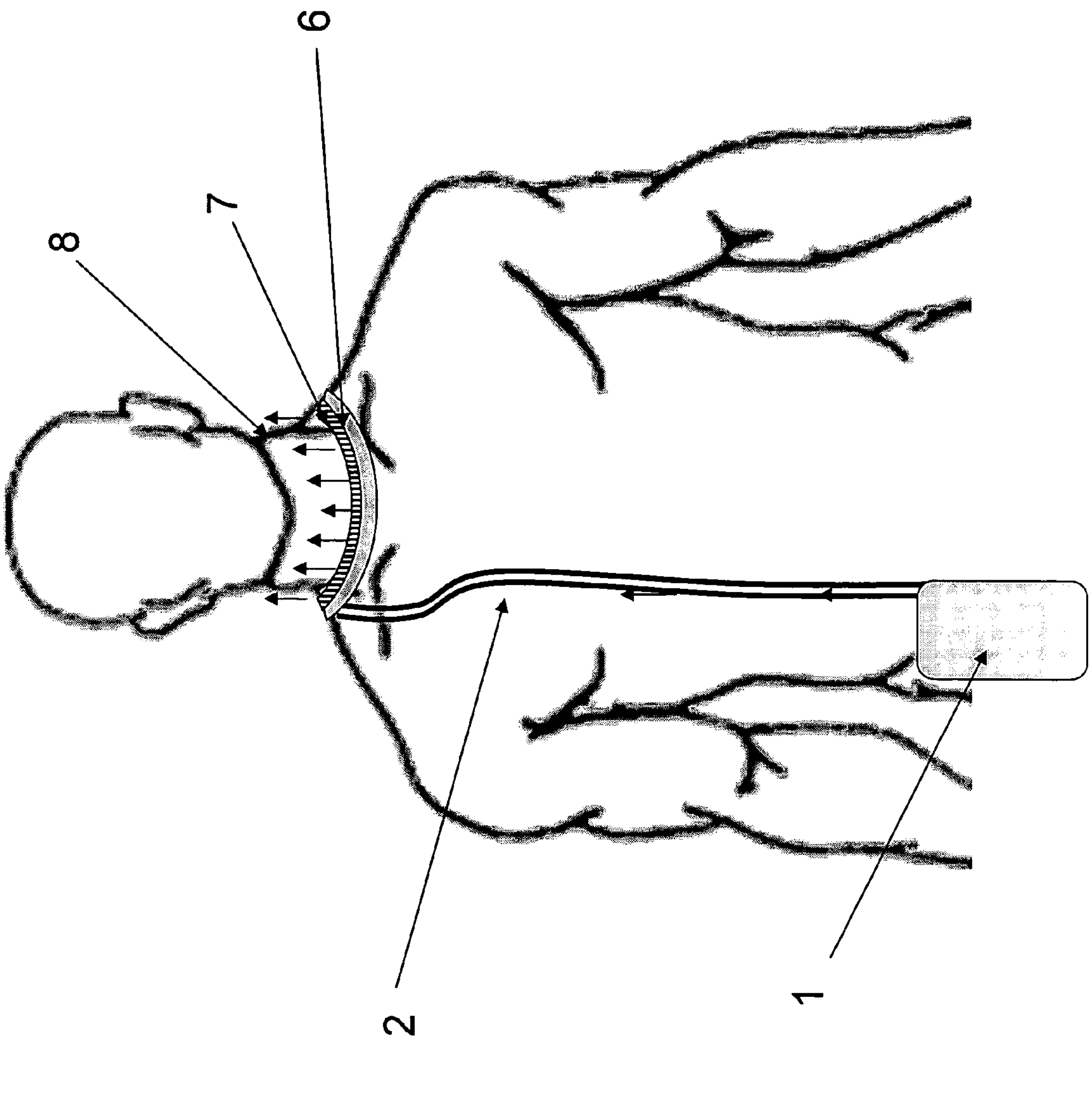
FIG. 2 is a perspective view of the neck-worn embodiment of the present invention.

FIG. 2 illustrates an alternative embodiment wherein the filtered air is channeled to the nasopharynx via a neck-worn garment 6 which in turn uses air channels 7 to create a pressure differential in the region of the nasopharynx 8. In this case, as well, only the positive pressure differential is illustrated although a negative pressure differential may also be used.

Figure 3:
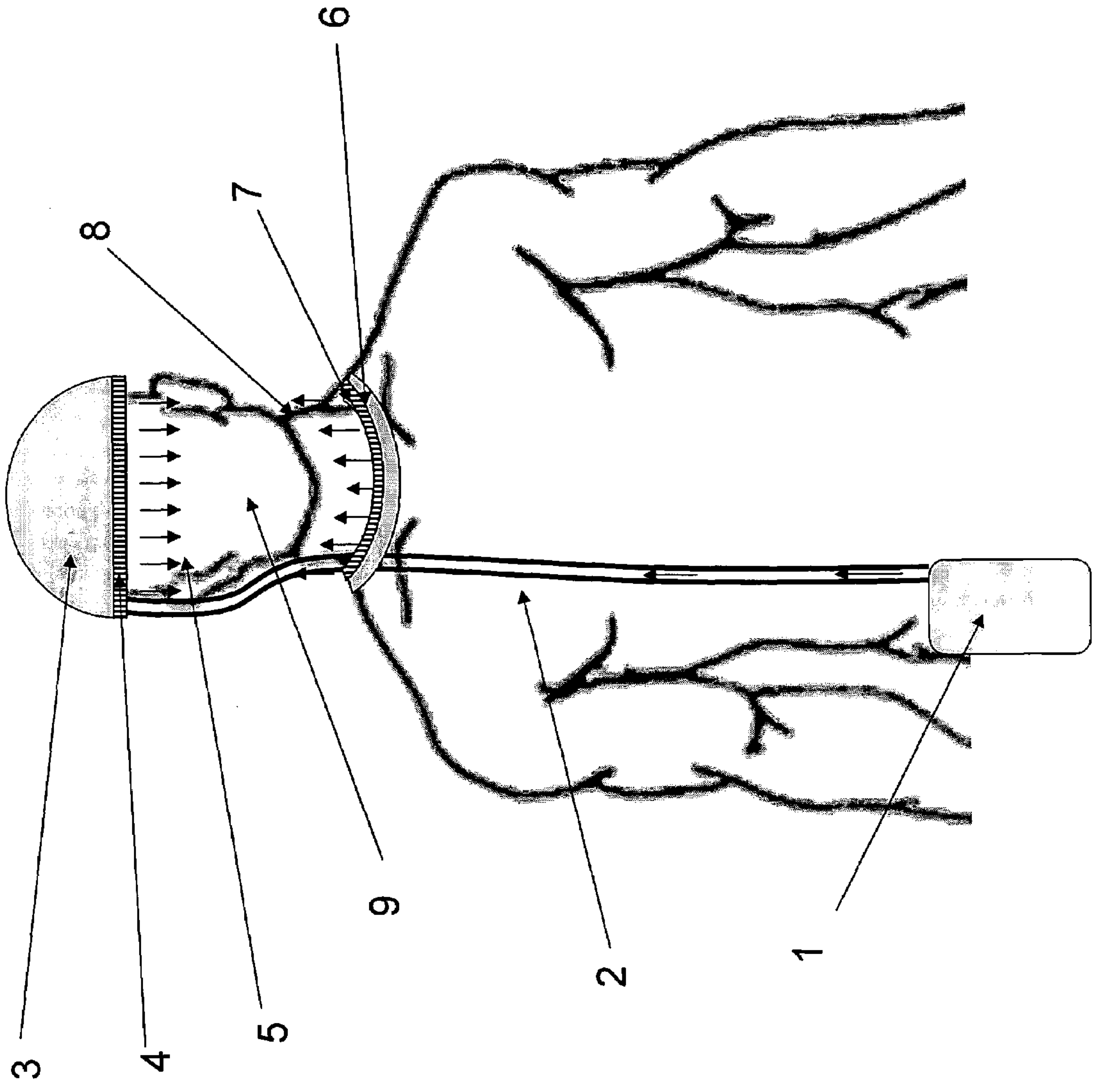
FIG. 3 is a perspective view of the combination cap- and neck-worn embodiment of the present invention.

FIG. 3 illustrates an embodiment wherein both the head- 3 and neck- 6 worn embodiments are used in order to create a pressure differential 9 in the region of the nasopharynx.

Figure 4:
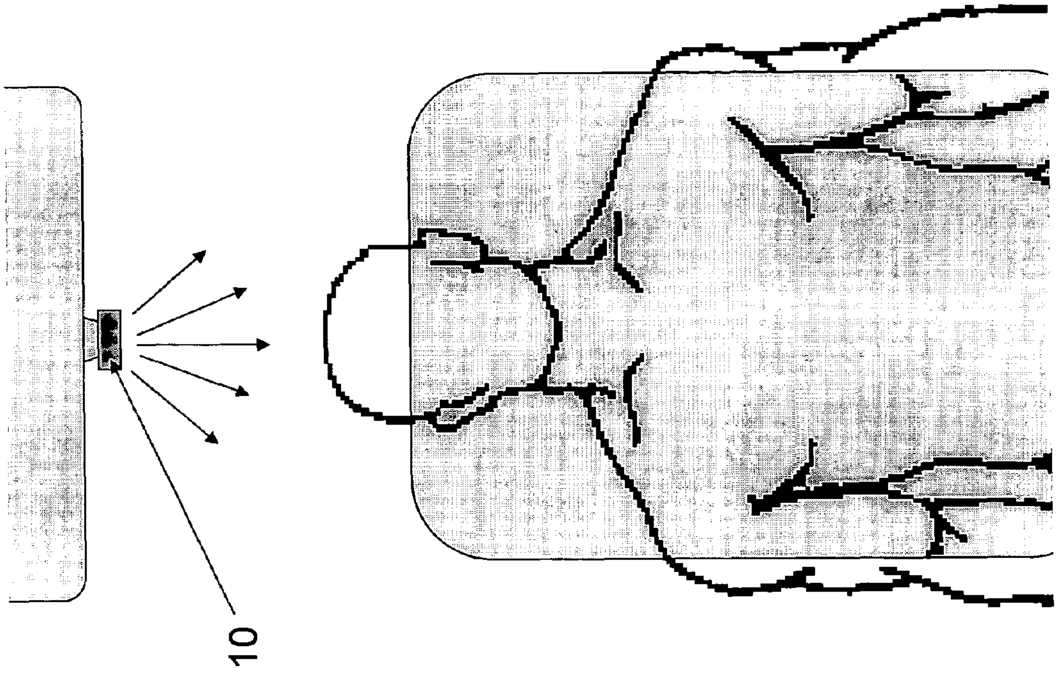
FIG. 4 is a perspective view of the positive pressure filtration cap embodiment of the present invention illustrated in a air travel setting.

FIG. 4 illustrates the use of an attachment 10 to an external pressure source, in this case the fan on an airplane, in order to generate the pressure differential required for positive pressure isolation.

Figure 5:
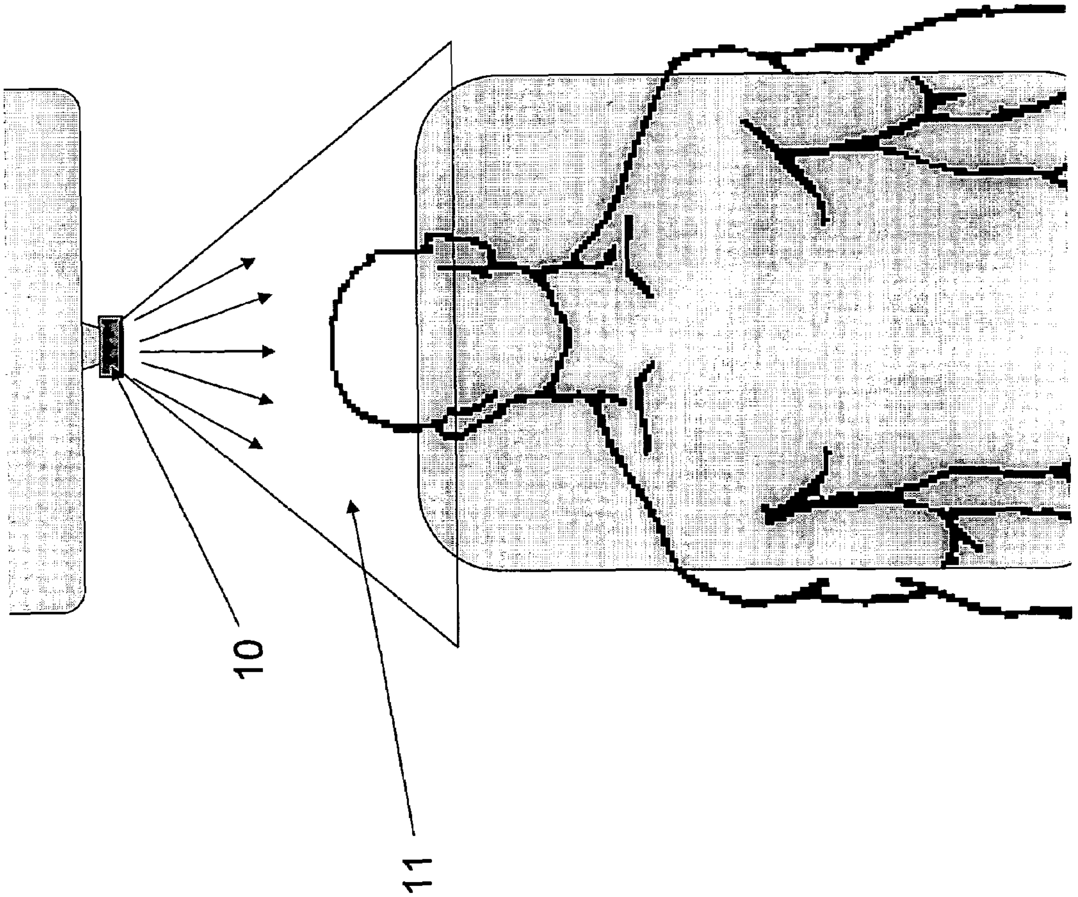
FIG. 5 is a perspective view of the positive pressure filtration cap embodiment of the present invention illustrated in a air travel setting with the optional canopy for improved positive pressure isolation.

FIG. 5 illustrates the same embodiment, but with the use of an exclusive canopy 11 to further isolate the user from their surroundings.

Figure 6:
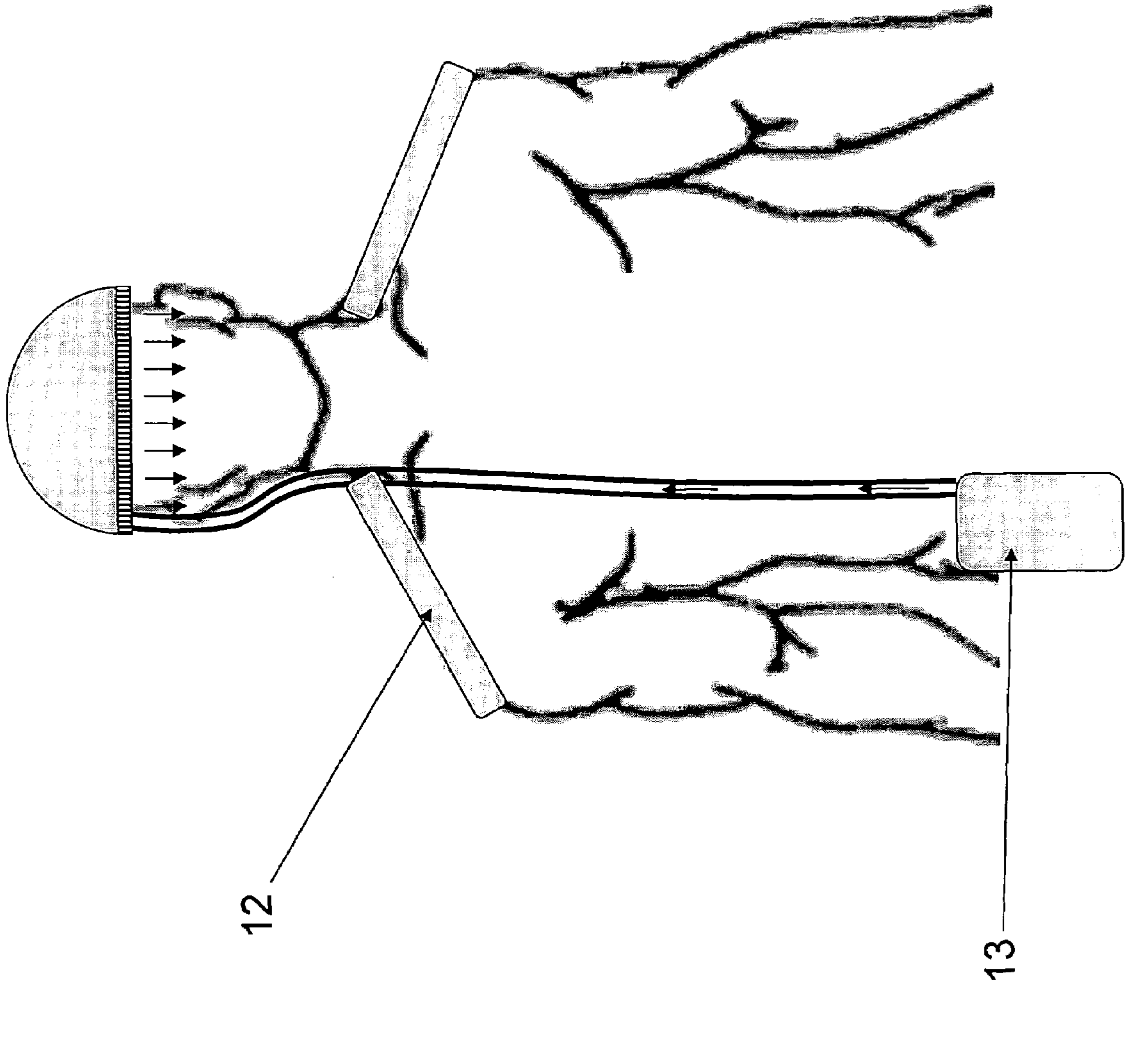
FIG. 6 is a perspective view of a full outdoor protection system including possible radiation exposure protection, positive pressure isolation and/or evaporative cooling.

FIG. 6 illustrates an embodiment capable of providing air filtration and/or evaporative cooling and/or protection from the external environment. In this embodiment, designed to protect the user from various hazards in their environment, the fan/filter 13 may also generate evaporated water in order to allow for cooling of the user. Furthermore, additional garments or outwear may also be used to protect the user from their external environment here illustrated as a mantle 12 over the users shoulders. In the illustrated embodiment, the user would be protected from all the hazards of the outdoor working environment, including exposure to toxins/pathogens in the air and/or exposure to excessive heat and/or exposure to harmful radiation.

Figure 7:
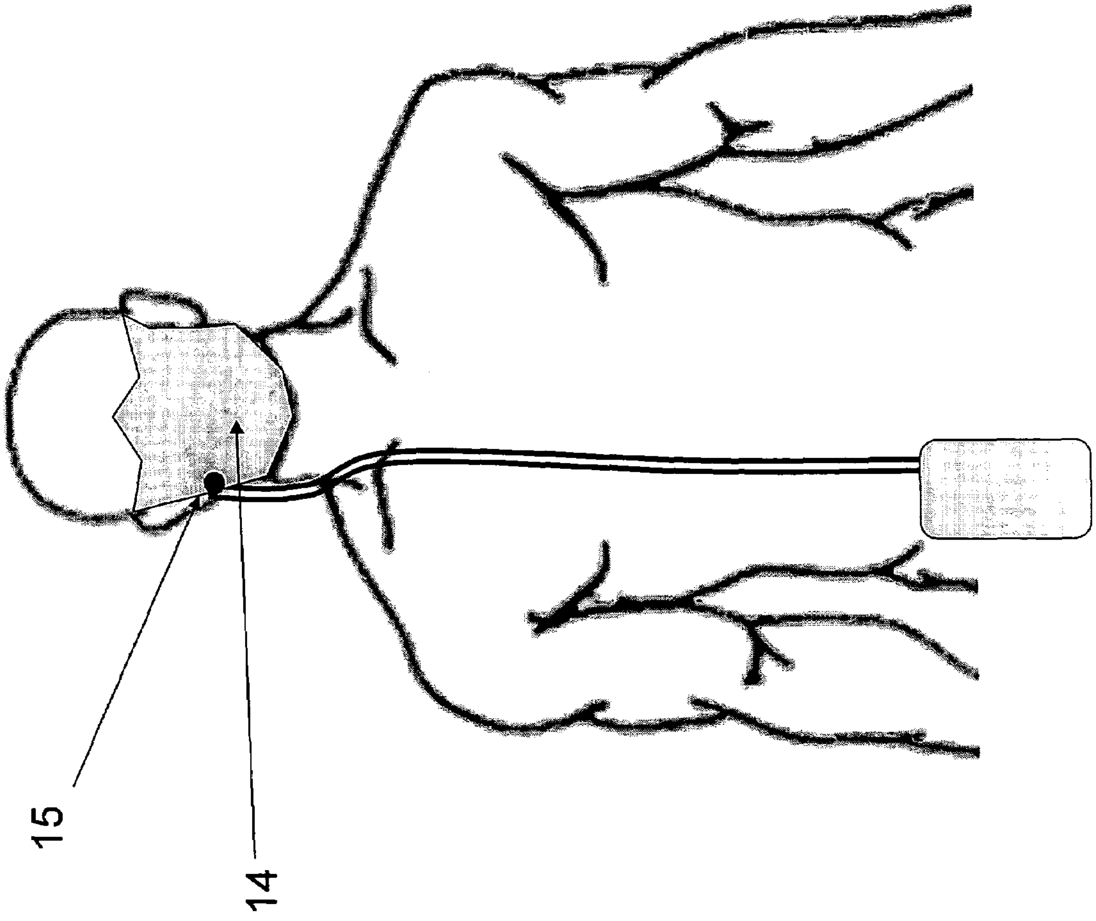
FIG. 7 is a perspective view of one embodiment of the present invention used in combination with a standard face mask to greatly increase effective isolation. Air flow may be to the face mask (to isolate the user from their surroundings) or from the face mask (to prevent transmission of pathogens from the user). In this embodiment, the face mask may form a seal around the user's nose and mouth or may allow air to enter or leave the region of the nasopharynx via the edges of the mask.

Lastly, FIG. 7 illustrates an embodiment designed for use with a standard or customized face mask 14. This embodiment may generate positive pressure under the mask (thus isolating the user from the environment) or a negative pressure (thus isolating the environment from the user). This design is ideal for healthcare workers and other users that desire vastly improved efficacy compare to a standard face mask. This embodiment may be used with standard face masks, may be manufactured as a single unit with the face mask attached or may require a face mask with an optional ventilation/air flow port 15. Anticipated, but not illustrated, is an optional air bladder which may be placed anywhere in line with the air flow path with the ideal embodiment having the bladder concealed down by the filter or fan. This bladder will allow a full, natural inhalation of filtered air without the need for excessive air flow during exhalation. This bladder, used in combination with a face mask and positive pressure maintenance between the face and the mask, will provide for a much more effective isolation. This bladder may be used with any of the embodiments and may be synchronized to inflate or deflate with the user's natural breathing.

What is claimed is:

1. An isolation and/or protection device comprising:

a portable pressurized air source; and a fluid delivery line having one or more channels defined therealong and fluidly coupled to the air source, wherein the fluid delivery line is configured for positioning in proximity to a nasopharynx of a subject while leaving a face of the subject unobstructed such that a localized pressure differential is created in a region of the nasopharynx by the fluid delivery line thereby fluidly isolating the region from a surrounding environment.

2. The device of claim 1 wherein said portable pressurized air source generates a positive pressure in the region of the nasonharynx.

3. The device of claim 1 wherein said portable pressurized air source generates a negative pressure in the region of the nasopharynx.

4. A method of isolating a user from their surrounding comprising:

providing a pressurized air source coupled to a fluid delivery line having one or more channels defined therealong, wherein the air source and fluid delivery line are portably carried by the user;

positioning the fluid delivery line in proximity to a nasopharynx of the user while leaving a face of the user unobstructed; and generating a localized pressure differential in a region of the nasopharynx through the fluid delivery line such that the region is fluidly isolated from a surrounding environment.

5. The method of claim 4 wherein providing comprises providing the pressurized air source to healthcare workers, immuno-compromised or otherwise susceptible patients, travelers, or construction works to limit exposure to toxins or pathogens.

6. The method of claim 4 further comprising evaporatively cooling the user through the fluid delivery line.

7. The method of claim 4 further comprising radiatively shielding the user through the fluid delivery line.

8. The method of claim 4 wherein positioning comprises integrating the fluid delivery line into garments or protective outerwear.

9. The device of claim I wherein the localized pressure differential is sufficient to repel airborne agents from the region.

10. The device of claim 1 further comprising a filter in fluid communication with the fluid delivery line.

11. The device of claim 1 wherein the fluid delivery line is configured for positioning upon a head of the subject superior to the face.

12. The device of claim 11 wherein the fluid delivery line is integrated with a headworn garment.

13. The device of claim 1 wherein the fluid delivery line is configured for positioning about a neck of the subject inferior to the face.

14. The method of claim 4 wherein generating comprises generating a positive pressure differential in the region of the nasopharynx.

15. The method of claim 4 wherein generating comprises generating a negative pressure differential in the region of the nasopharynx.

16. The method of claim 4 wherein positioning comprises positioning the fluid delivery line in a position superior to the face of the user.

17. The method of claim 4 wherein positioning comprises positioning the fluid delivery line in a position inferior to the face of the user.

18. The method of claim 4 wherein generating a localized pressure differential comprises repelling airborne agents from the region.

19. The method of claim 4 further comprising filtering air removed from the region.

* * * * *